Figure 1:

United States Patent [19]
Raybuck et al.

[11] Patent Number: 5,447,864
[45] Date of Patent: Sep. 5, 1995

[54] CAPTURE METHOD FOR CELL NUCEI USING A DNA MESH

[75] Inventors: Margaret P. Raybuck, Pontyclun Mid Glamorgan; Michael K. Kenrick, Cardiff, both of Wales; David A. Parry, London, England; Andrew L. Bertera, Newport, Wales; John G. Anson, Cardiff, Wales; Nicola M. Williamson, Cardiff, Wales

[73] Assignee: Amersham International Limited, United Kingdom

[21] Appl. No.: 120,530

[22] Filed: Sep. 14, 1993

[30] Foreign Application Priority Data

Sep. 18, 1992 [EP] European Pat. Off. ........... 92308537

[51] Int. Cl.[6] .............................................. C12N 1/06
[52] U.S. Cl. ...................................... 435/270; 435/2; 435/174; 435/177; 435/178; 435/179; 435/180; 435/181; 435/182; 435/240.1; 435/243; 435/259; 435/267; 435/317.1; 435/803; 435/820; 436/63; 436/176; 436/177; 436/178; 536/22.1; 935/19
[58] Field of Search .................... 435/2, 173, 174, 177, 435/178-182, 240.1, 243, 245, 267, 270, 317.1, 803, 820, 259, 176; 436/8, 63, 174, 175, 177, 178, 176; 536/22.1; 935/19, 85

[56] References Cited

U.S. PATENT DOCUMENTS

4,668,618 5/1987 Thornthwaite ........................ 435/6

FOREIGN PATENT DOCUMENTS

0312394 4/1989 European Pat. Off. .
8809201 12/1988 WIPO .

OTHER PUBLICATIONS

Leadon et al., Analytical Biochemistry, 120 (2), 282-288; (1982).

*Primary Examiner*—Margaret Parr
*Assistant Examiner*—Ardin H. Marschel
*Attorney, Agent, or Firm*—Wenderoth, Lind & Ponack

[57] ABSTRACT

A method of separating cell nuclei from cells comprises: treating a fluid containing whole cells so as to selectively lyse the cytoplasmic membrane together with a small proportion of the nuclear membranes but leaving a large proportion of the cell nuclei intact; applying the treated fluid to a membrane whereby a mesh of DNA from the lysed nuclei is formed on the surface and captures intact cell nuclei. A device for use in the method is described.

9 Claims, 2 Drawing Sheets

CAPTURE METHOD FOR CELL NUCEI USING A DNA MESH

BACKGROUND

Preparation of cell nuclei is desirable for a number of subsequent applications. These include studies relating to the mechanisms of transcription in the cell. The nuclei are used to contain trans-acting factors and necessary enzymes and cofactors to allow transcription to occur in in vitro reactions. Soluble extracts from nuclei preparations are useful for both trans-and cis-acting element study as well as being useful for purification and physical characterisation of the factors.

The first report of the use of nuclear extracts was reported in 1983 (Dignam et al N.A.R. 11: 1475-1489) and these have now become standard practice. These methods take 3-4 hours to prepare the nuclei however, involving two spins in an ultra centrifuge using density cushions. The clean intact nuclei are then made into extracts after lysis for their use in experiments such as G-free cassette, (Sawadogo and Roeder P.N.A.S. 82 4394-4398, 1985), primer extension, RNAse mapping, S1 nuclease etc. These traditional methods of nuclei isolation are laborious, slow and limit the number of samples which can be handled at a time. They also compromise the quality of the final lysate in that the nuclei are in the process for long periods during which time many useful factors can leach out or be denatured.

Generally the generation of nuclei is performed by selective lysis of cell cytoplasm by osmotic shock, mechanical shearing and differential centrifugation so the nuclei are the only items to sediment. These processes are very difficult to implement especially in complex biological samples and proscribes against the processing of large numbers of samples and automation. Consequently nuclei preparations are only done when there is no other alternative method although reports in the literature have stated that the quality of DNA derived from purified nuclei is superior to DNA extracted by other means. (A Laboratory Guide for In Vivo Studies of DNA Methylation and Protein/DNA Interactions: Biomethods vol 3 ed. by H. P. Saluz, J. P. Jost 1990 pub. by Birkhauser Verlag).

For the vast majority of procedures in both research and diagnostic molecular biology extracted nucleic acids are required as the first step. For example, relatively pure samples of genomic DNA are required to perform tests for genetic diseases and for recombinant DNA technology the DNA to be cloned must be purified. In the detection of infectious disease organisms such as viruses, access to the cell DNA is necessary where many of these microbes lie hidden.

To avoid the meticulous and lengthy procedures of nuclei preparation, extraction of DNA is commonly done by complete initial release of the DNA by disruption of cytoplasm and nucleus as the first step. This can be done by freeze-thawing, ultrasound, shearing, enzymes, chelating agents or surfactants. DNA is not found as free molecules in a cell nucleus but exists as a complex association of DNA, RNA and proteins. Most DNA extraction techniques use degrading enzymes for major protein and RNA removal followed by repeated solvent extraction with phenol and alcohols to remove residual contaminating proteins and other macromolecules.

These processes are labour intensive, require the use of hazardous, volatile solvents and because of the number of manipulation steps can result in the relatively fragile genomic DNA being broken into small pieces. For many procedures large fragments are necessary (see below). Standard nucleic extraction procedures are mentioned in reference Sambrook et al Molecular Cloning A Laboratory Manual 2nd edition 9.14 (New York: Cold Spring Harbor Laboratory 1989), These involve lysis of cells, enzyme digestions, repeated phenol/-chloroform extractions and dialysis, the whole procedure taking many hours. There has been considerable work on developing improved extraction procedures which avoid the use of organic solvents. These include use of chaotropes such as sodium chloride, sodium perchlorate, lithium chloride. [Grimberg J. et al N.A.R. 17, 8390 (1989), Buttone G. J. and Darlington G. J. Clin. Chem. 31, 164-165 (1989), Johns, M. B. and Paulus-Thomas J. E. Anal. Biochem. 180, 276-278 (1989), Miller S. A. N.A.R. 16, 1215 (1988)]

Patents EP-A-0 145 356 and EP-A-0 240 191 and EP-A-0 245 945 describe extraction methods all of which involve alcohol extraction. DNA extraction from blood samples is particularly troublesome as an extra step of separating out the white cells from the vast excess of red cells and serum proteins is usually necessary. This is done by centrifugation either to isolate the buffy coat fraction or to pellet the nuclei after cellular lysis.[Grimberg J. et al N.A.R. 17, 8390 (1989)]

Recent developments for amplification and detection of nucleic acids using polymerase chain reaction and other amplification methods require purified or extracted DNA to a different specification. Patent numbers U.S. Pat. No. 4,683,195 and U.S. Pat. No. 4,683,202 describe amplification and detection procedures for nucleic acids found in various biological specimens using a polymerase. Although DNA for amplification often does not need such thorough purification as for other applications there are other important requirements for blood DNA samples such as the efficient removal of haemoglobin. This and other inhibitory substances in blood must be removed to avoid inhibition of the polymerase enzymes.

This is particularly important in performing quantitative amplifications where changes in the efficiency of the reaction may well give spurious results. In fact such a nuisance is this that considerable work has gone into discovering enzymes which are less affected by inhibition of blood components. In addition denaturants such as phenol which are very common reagents in DNA extraction are extremely inhibitory to enzyme reactions of all types.

With this in mind methods have been devised to avoid phenol extractions during nucleic acid purification. For example Kogan et al N. Eng. J. Med., 317 16 985-990 (1987) describe extraction of DNA from cells previously separated centrifugally from whole blood by boiling. Others describe similar procedures in EP-A-0237 362 and in Saiki et al Nature, 324, 163-166 (1986). These methods still imply pre-treatment of the whole blood by the rate limiting step of centrifugation and also do not provide the means for the thorough removal of factors found in blood such as haemoglobin which can be very inhibitory to amplification reactions.

Also while seeming to be reasonably quick and easy they are largely useful only for situations where the samples are relatively large. Patent EP 0 393 744 A1 describes yet another version of this which still requires white cell centrifugation and involves adding polysaccharides during the boiling step.

Yet more of a shortcut is the spotting of blood onto filter paper and allowing it to dry. These have been utilised in hospitals for years as "Guthrie" spots and are for the original purposes of screening neonates for disorders such as phenylketonuria, hypothyroidism and galactosemia. A paper reports the extraction of DNA from Guthrie spots by extraction into methanol and subsequent enzyme and phenol/chloroform treatments and also direct amplification by PCR on the membrane after cutting out the spot and fixing with methanol. {McCabe, E. R. B. PCR Methods and Applications 1(2) 99-106 (1991)}. This paper also describes in great detail the need for methods of DNA extraction which lend themselves to non-laboratory collection points without compromising the quality of the result.

This is particularly relevant with neonatal screening programmes, forensic samples, infectious disease situations and agricultural applications in both developed and developing countries world-wide.

For diagnostic testing to be commercially feasible it must also be economically efficient. Each stage must be simple, easy-to-use and consequently safer with respect to possible laboratory infections from occult infectious agents especially in blood, blood products and tissues. The amount of blood or other body fluid contaminated waste must be kept down to a minimum as disposal is difficult and expensive. There is also a need for rapid processing to allow early clinical decisions.

In many clinical samples the sample size is very restricted either due to the moribund state of the patient, the sample origin such as foetuses, amniocentesis samples, cerebrospinal fluid, etc. Also there are many instances where the cells containing the DNA are at low concentration such as in immunosuppressed patients or where the cells are a rare population such as foetal cells in the mothers bloodstream. Further examples of this are in virus infections such as HIV where the virus DNA loading may be extremely small (1 in a million cells for example) but it is still extremely important that this infected cell is found for a correct diagnosis.

Other methods of DNA extraction are employed when it is vital that the DNA remains in relatively large pieces. The largest requirement for synthetic chromosome work requires pieces thousands of megabases long. Other cloning systems need sizes from 50 kb up to 500 kb the larger being the better in many cases as it reduces the total number of clones to cover the entire genome of 3000 megabases. As the entire stretch of DNA within a cell reaches for over 20 metres when released from its protected position within the nucleus it becomes very vulnerable to breakage during pipetting, centrifugation or any other manipulation. Methods have been developed which enclose cell suspensions within agar blocks or sheets and then lysis of the cell cytoplasm and nucleus occurs within the blocks by diffusion of surfactant etc. Other treatments such as enzyme reactions also occur by diffusion within the block so stressing of the DNA is kept to a minmum. Electrophoresis can then be done without any stressful manipulations of the DNA. In this way megabase-sized DNA can be produced for subsequent restriction down to the required size if smaller. McCormick, M. K. et al. P.N.A.S. 86 9991-9995, 1989.

For very delicate, large constructions of DNA such as yeast artificial chromosomes it is crucially important to prevent any breakage during handling. This is done by embedding the DNA within agarose blacks so that it is supported at all times. These agarose plugs can then be placed on an agarose gel and electrophoresis performed as normal for very large DNA samples. [Smith, D. R. et al. P.N.A.S. 87 8242-8246, 1990].

Nuclei isolation is commonly done for a variety of other molecular biology techniques. It has been employed to remove a major source of contamination for mRNA purification. This is an improvement over traditional methods for DNA removal which involve either DNAse treatment which then has to be removed, or guanidinum salts to disrupt the cells followed by physical shearing of the DNA. [Current Protocols in Molecular Biology. Ausubel, F. M. (1988) pp 4.1.2-4.1.6. Wiley, N.Y.]

Other uses for nuclei are, DNA-binding protein studies, in situ hybridisation, transcription studies, nuclear cage studies etc.

Attempts to obtain high molecular weight DNA have been reported. A procedure has been suggested where whole cells are lysed in situ on the membrane and mentions that previously isolated nuclei could also be used though it doesn't say how these nuclei would be prepared, nor is any work reported on this. [Leadon, S. A. and Cerutti, P. A. Anal. Biochem. 120 282-288 (1982)] This paper describes a process where cells are lysed, digested and washed on a polycarbonate filter, allowing contaminating material to be washed off.

The method suggested consisted of the filtration of the nuclei or cells through pores of a much smaller size or simply the drying down of the nuclei onto filter paper. In the first case the amount of nuclei which can be captured is very limited as the pores very quickly block up. Also it is not possible to wash away contaminants very thoroughly due to the nature of the capture. Vigorous washing would remove the nuclei especially if the loading was so great that most of the pores were blocked. Other procedures based on the same principle have a subsequent dialysis stage to selectively remove small cellular contaminants. [De Klowet, D. et al J. Microbial Methods 2. 189-196 (1984)]

These do not involve any specific capture mechanism but rely on non-specific filtration and trapping. The purpose of these methods is to preserve the DNA in an intact form so that any cutting is by design and not due to non-specific breakage during preparation. Similarly there is patent no. JP 2295485 which describes whole blood cell capture by filtration through mesh with pore size smaller than 10 micron. They claim that absorption into the pores of the mesh allows the haemoglobin to be efficiently washed away.

There have appeared in the last few years several new formats for affinity chromatography based on filtration membranes especially for antibody purification. Most commonly these involve the use of a filtration cartridge format, familiar to those working in biological fields. This consists of either a disposable or reusable cassette within which is mounted a disc of filtration membrane.

The membrane is supported on both sides by plastic meshes within the cassette and leading out from the upper and lower surfaces of the cassette is a nozzle designed to be attached to a syringe and an outlet designed to be directed into the collection vessel. These cassettes sometimes include in the design, channels of liquid flow to maximise the interaction of the fluid across the membrane. (U.S. Pat. No. 4,690,757).

Later developments have lead to new versions with either capture moieties already permanently attached or in a chemically activated form for custom derivatisation. The discs are usually about 5 cm in diameter and are claimed to have as high a binding capacity as a column. This is consistent with their use with a syringe for the application of large samples of between 1 and 50 mls of solution at a time.

As these cartridges are contained it is not easy to see when they are full of liquid and this can result in air being drawn through and partial drying out of the membrane in an attempt to reduce the minimum volume. Also because the membranes are contained and supported it is not easy to remove the membrane for visualisation either by light electron microscopy. Similarly they cannot easily be used for subsequent reactions. Some of the cartridges can be disassembled and hence the membrane removed. The true purpose of this is re-use of the cartridge however and usually results in some damage to the membrane.

The concept of effecting separation on the end of a tip has been utilised before in patent No. WO8809201. In this case however the tip contains column material between two frits and is therefore a miniature column.

THE INVENTION

This invention provides a method of separating components of cells, which method comprises
a) treating a fluid containing whole cells so as to selectively lyse the cytoplasmic membrane together with a small proportion of the nuclear membranes but leaving a large proportion of the cell nuclei intact,
b) applying the treated fluid to a surface whereby a mesh of DNA from the lysed nuclei is formed on the surface and captures intact cell nuclei,
c) washing the DNA mesh on the surface to separate the captured cell nuclei from other components of the cells.

The invention also provides a device for use in the method, comprising a tube which is open at its rearward end and has a filter element extending across its forward end, the tube having between its ends a circumferentially-extending peripheral line of weakening and being made from a brittle plastics material whereby the tube can be broken along said line of weakening, said filter element providing the surface on which the mesh of DNA forms.

The first stage of the method is the selective lysis of the cytoplasm of whole cells. Typically this is performed using a mild detergent and (buffer) salt concentration to produce an osmotic shock.

There may or may not be additional reagents such as sucrose to cushion the revealed nuclear membrane. The literature has a wealth of methods for all types of cell and tissue, so that a skilled reader will have no difficulty in choosing a suitable method. The idea of the method is to burst only a very few of the nuclei, releasing their total DNA which then forms a coarse mat which traps and supports the unlysed nuclei.

It has been shown that even under very mild conditions there is a gradual lysis of isolated nuclei starting at a few minutes and going on for up to several hours (Thomas, N., PhD Thesis, Subcellular localisation and Function of Glucocorticoid Receptors, 1982).

The nature of the cells is not critical to the invention. Nucleated cells from any source, including plant cells and animal cells can be used, though the invention is likely to be of particular value for the recovery of genomic DNA from whole animal blood and tissue. Methods of selective lysis are known for cells of any source including insects, yeast, invertebrates, chicken erythrocytes, plant cells etc.

The chosen buffer must be appropriate for a) the selective lysis of the cytoplasmic membrane without damaging the nucleus and b) allowing the lysis of sufficient nuclei to form a capture web. Depending on the type of nuclei in question, different buffers are required. This is because some nuclei are much more resistant to lysis than others. In addition there are variations in efficiency of capture due to degree of lysis allowed. For example, cultured cell lines have nuclei which are very resistant to lysis. There is substantial scope for optimisation. If it is most important to preserve nuclei in good condition, then minimal lysis may be chosen at the expense of maximal capture. If it is important to capture as much nuclear DNA as possible, then increased lysis of cell nuclei may be appropriate.

Other factors which can contribute to the degree of lysis are mechanical action, such as passing the fluid through a membrane with more or less vigour, and the length of time the cells are exposed to the lysis solution. All these factors need to be optimised for the best results for each new cell type used.

The treated fluid is then applied to a surface. All, or more usually part, of the DNA from the lysed nuclei forms a mesh which remains in contact with the surface and captures intact cell nuclei. The surface preferably takes the form of a permeable membrane, that is to say a membrane through which the treated fluid can be passed. Membranes of woven or non-woven fibres or filaments are preferred. However track etched or other methods of filter manufacture are also suitable. Alternatively, solid sheets can be used. The choice is dependent on the particular application. Membranes of various pore sizes are also suitable; the larger the pore size, the easier removal of contaminants becomes, but the less is the retention of the nuclei because there are fewer positions for attachment of the DNA mesh.

Various means are available for ensuring that the mesh of DNA remains in contact with the surface. Preferably the surface is of a material which is capable of binding DNA, for example by chemical interaction or hydrophobic bonding or physical absorption or by a charge interaction. DNA binding to plastics materials is complex and involves various combination of these phenomena. For example a highly charged polymer surface may favour charge interaction, while an uncharged polymer surface may favour hydrophobic bonding. When the surface is a permeable membrane, the DNA mesh may be physically trapped on or in the pores or apertures of the membrane. It is alternatively possible, but not preferred, to use a surface which has no nuclear capture properties; for example, a DNA mesh could be sandwiched between two permeable membranes.

Many materials are known which have nuclear capture properties, including polyester, polyamide, polycarbonate, cellulose, nitrocellulose, polyvinylidene difluoride, and glass. These are preferably used in the form of porous membranes of woven or non-woven fibres or filaments, such as are commercially available. Or the surface can be made of any material which can be activated chemically or physically such that it binds DNA, for example by having positive charges attached or by concealing negative charges, or by the addition of hydrophobic binding moieties.

The structure of the assembly for the support of the permeable membrane or other surface is not critical to the invention. This can be part of a filtration unit, or be attached to a carrier in the form of a 'dipstick'. Also, the method for applying the treated fluid to the permeable membrane or other surface is not critical to the invention. It is possible to use a pumped system, with either positive or negative pressure, or simply to allow settlement of the DNA mesh on the surface during an incubation.

It is a characteristic feature of the invention that intact cell nuclei are captured by a DNA mesh rather than by any other form of nuclear capture surface. It is the DNA mesh that is generally absorbed or bonded on the surface. Generally the DNA for the mesh is present or is formed in the fluid at a time not later than the fluid is applied to the permeable membrane or other surface. In this context, however, steps a) and b) of the method of the invention can be performed simultaneously.

Once capture of the nuclei has been effected, the lysis agent can be removed by usual washing techniques. Thus the permeable membrane or other surface (with the DNA mesh and nuclei attached), can be immersed in a washing solution, or a washing solution can be passed through the permeable membrane. Washing solutions and techniques are not critical to the invention.

The method of the invention is preferably used to separate and recover cell nuclei and associated DNA from other cellular contaminants. However, the method can also be useful for the removal of nuclear components to allow recovery of the cytoplasmic fraction. This has the same advantage as for DNA, but the whole process is so rapid that potentially labile cytoplasmic components can be obtained in good condition.

For these applications also, the detergent/buffer solution needs to be optimised, as some detergents/buffers may damage components of interest. Varying the pH/ionic strength/ion type/detergent type/detergent concentration and time of lysis can adapt this method for all further applications.

For removing nuclei from the permeable membrane or other surface, several methods are available depending on the desired application.

If large intact DNA is required removal of the nuclei must be by the use of either non-sequence specific DNAses or sequence specific restriction enzymes which are immobilised on a solid phase such as a bead. This is because the nuclear membranes are very permeable and will allow these enzymes to enter and degrade the internal DNA. It may be possible also to effect the same by removing the DNAse after a short period by washing to cut the exposed DNA before much entry into the cells has occurred.

In either case the nuclei can then be washed off or centrifuged off the membrane.

If restricted DNA is required then restriction can go ahead on the mesh. The capture-DNA will be cut as well as intranuclear DNA. The nuclei/cut DNA can then be eluted by washing or centrifugation.

If intact nuclei are required then they must be returned quickly after capture to a supporting medium containing glycerol or sucrose without detergents to prevent loss of internal components such as transcription factors.

The nuclei can then be removed by either of the above methods for further treatment.

DNA and or nuclei can also be stored for long periods on the membrane either by drying, freeze-drying or freezing at either −20 or below. For short period storage they can be kept at 4° C.

For maximum preservation of ultra-large DNA the nuclei can be left on the membrane and placed either in low-melting agarose blocks for lysis in situ or added straight to the electrophoresis gel to be electro-eluted; this is especially important in connection with pulse-field electrophoresis or variants such as CHEF etc all of which have pulsating, varying and reversing electric fields to separate large DNA fragments.

Reactions such as PCR can be performed on the membrane with no inhibition of the reactions. The coarseness of the mesh allows free interaction of the components. Materials must be chosen however to avoid inhibitory effects of some plastics.

Reference is directed to the accompanying drawings, in which FIG. 1 is an electron micrograph showing goat blood nuclei trapped in a mesh of DNA on a solid surface. Briefly, blood lysed by sucrose/triton (to produce nuclei) was aspirated through a polyester membrane and subsequently washed and stored in phosphate-buffered saline. The membrane was dehydrated by sequential exposure to increasing concentrations of ethanol and then fixed with glutaraldehyde, freeze-dried, mounted and sputter-coated with gold. This is an standard E.M. preparative technique. The micrographs were produced by Scanning E.M. at the indicated magnification. Cell nuclei are clearly visible as discs a few mm in diameter. The DNA mesh, on which the nuclei are trapped, is also clearly visible as pale lines to some extent tangled together. The grey background is the surface to which the DNA mesh is attached.

Figure 2:
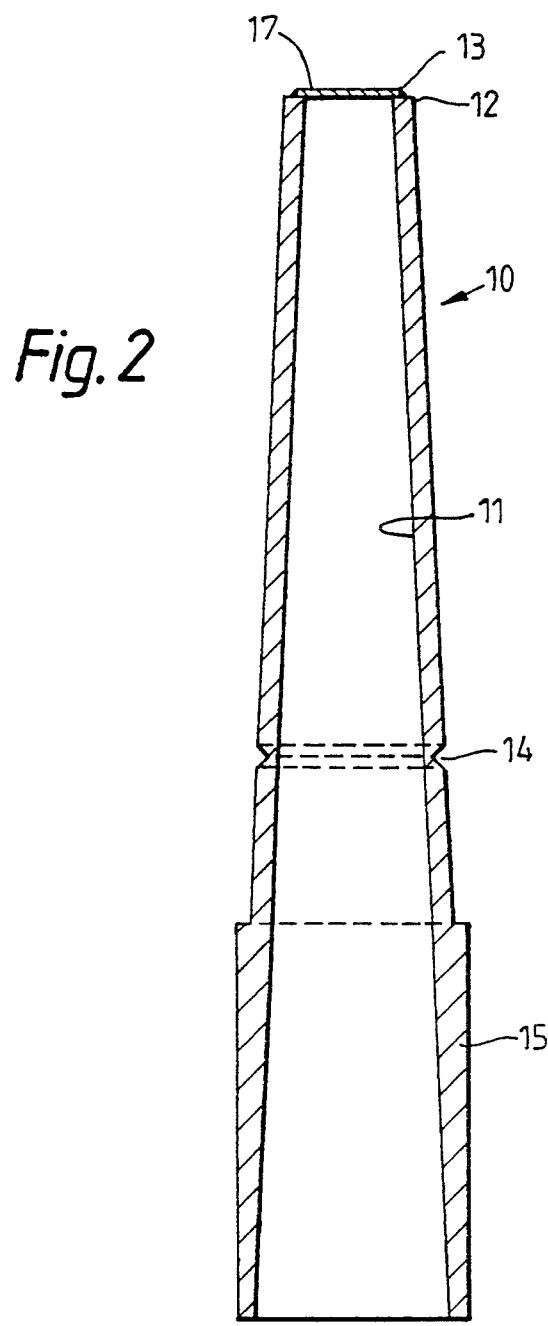
Figure 3:
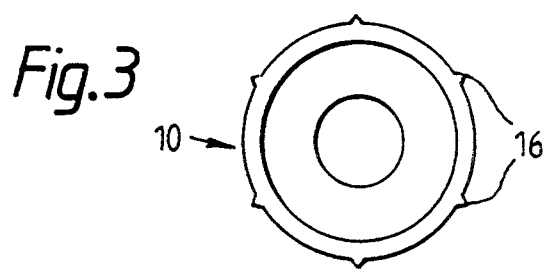

FIGS. 2 and 3 of the drawings show sectional and end elevations respectively of a preferred form of device for use in the method as a means of capturing the cell nuclei.

The device comprises a tube 10 the bore 11 of which decreases in diameter along its length towards its forward end 12. The forward end face of the tube has an annular pip 13 for the attachment of a permeable membrane or other filter element extending across the bore and selected according to the nature of the nuclei to be captured. The pip has in this construction a triangular cross-section. A line of weakening in the form of a peripheral groove 14 is formed in the wall of the tube at a selected distance from the forward end. In its rearward end portion 15 the external surface of the tube is cylindrical and has a series of axial stiffening ribs 16 to enable that end of the tube to be secured in a friction fit on the end of a micro-pipette. The tube is made from a transparent and brittle thermoplastic plastics material. Polycarbonate is particularly suitable for this purpose.

In use of the device, a mixture as described in the Examples is drawn by the micro-pipette through the membrane which is selected according to the nature of the nuclei to be captured. The captured DNA mesh is then washed by drawing a wash solution through the membrane and the tube is then broken at the line of weakening at the whole forward end part of the tube with the membrane and captured DNA is placed in a standard Eppendorf tube containing a standard reaction mix for PCR amplification. To enable the lid of the Eppendorf tube to be closed it is particularly advantageous for the groove 14 to be formed at a distance of 18 mm from the forward end of the tube.

An aerosol filter is preferably provided between the tube 10 and the micro-pipette to prevent contamination of the latter.

The polycarbonate material from which the tube is made should be in accordance with certain stringent requirements. Thus it should withstand autoclaving at 120° C. for 20 minutes and repeated heating and cooling between 95° C. and ambient temperature. The material must not inhibit enzyme reactions such as PCR either by removal of crucial factors by absorption or chemical inhibition by its surface chemical nature or added constituents. The material should preferably not fracture on freeze-thawing.

In manufacture of the tube, no plasticizers or mould release must be used.

Reference is directed to our patent application, filed on the same date as this one, entitled "Capture Device". That patent application relates to a device for capturing a component present in a biological fluid, comprising a tube having a rearward end adapted to be fitted to a pump for drawing fluid through the tube, and a forward end, with at least one membrane extending across the tube at or adjacent its forward end. That device is suitable for use in the method of this invention.

EXAMPLE 1

Preparation of nuclei of "Southern-blot" quality.

An equal volume of the following buffer is added to fresh whole human blood taken in citrate coated tube (anticoagulant):

10 mM Tris pH 8.0
320 mM sucrose
5 mM $MgCl_2$
1% (v/v) Triton X-100

The buffer is incubated at room temperature for 5 minutes to lyse red cells and white cell cell membranes and a few nuclear membranes.

The mixture is collected by pulling through a 5 mm disc of 1 micron pore size polyester which traps and binds the mesh comprising DNA. This is done using a syringe.

The mesh is washed by pulling through wash solution: 2×1 ml phosphate buffered saline followed by one wash in distilled water.

The membrane on which the mesh is still held is then touched onto the surface of the following liquid which bursts the nuclei: A minimal amount of liquid is needed:

20 mM Tris pH 8.0
1 mM EDTA pH 8.0
0.5% (w/v)SDS
1 mg/ml proteinase K
0.4 mg/ml RNAse A
0.4 U/ml RNAse T1

The membrane is then put into an Eppendorf tube and is incubated at 55° C. 30 mins followed by 80° C. 10 mins.

A 30 second spin removes the purified DNA from the membrane.

Standard procedures are followed at this point of phenol/chloroform extraction and ethanol precipitation to remove contaminating proteins and detergent which might inhibit subsequent restriction enzyme reactions.

DNA made in this way digested with 10 different enzymes showed equal cutting between traditionally made DNA and mesh-capture DNA.

Those digests were probed with a "defensin"0 probe to show that the quality of a Southern blot is the same for mesh DNA as well as standard DNA. DNA "fingerprint"0 banding patterns were identical between controls and DNA derived from mesh captured nuclei.

EXAMPLE 2

An equal volume of the following buffer is added to fresh whole human blood taken in citrate coated tube (anticoagulant):

10 mM Tris pH 8.0
320 mM sucrose
5 mM $MgCl_2$
1% (v/v) Triton X-100

The buffer is incubated at room temperature for 5 minutes to lyse red cells and white cell cell membranes and a few nuclear membranes.

The mixture is collected by pulling through a 5 mm disc of 1 micron pore size polyester which traps and binds the DNA mesh. This is done using a syringe.

The mesh is washed by pulling through wash solution: 2×1 ml phosphate buffered saline followed by one wash in $dH_2O$.

The mesh is then added still attached to the membrane to an Eppendorf tube containing a standard reaction mix for PCR amplification. In this example it was:

5 μl 10×PCR buffer (100 mM Tris, 15 mM $MgCl_2$, 500 mM KCl, pH9.0)
5 μl 3H dNTP mix (1Ci/mmol) 200 μM dATP,dCTP, dGTP,TTP, +1 μCi 3H-TTP
0.1 μl primer 1 (50 μM)
0.1 μl primer 2 (50 μM)
0.4 μl Taq polymerase (50 μl)
0.5 μl gelatin (10 mg/ml)
33.9 μl sterile water Total volume 45 μl The membrane is added to keep below the surface of the liquid and 2 drops of mineral oil are added.

The following cycle programme was used:
95° C.–30 secs
55° C.–120 secs
72° C.–180 secs 40 cycles
95° C.–30 secs
55° C.–120 secs
72° C.–600 secs
40° C.–indefinite After the reaction a sample was run on an agarose gel.

Amplification of DNA between the primer set was shown to be efficient with membrane captured nuclei and compared favourably with nuclei that had been washed several times with saline by resuspension and centrifugation. One hundred microlitres of a 100-fold dilution of blood (with saline) that was aspirated through a 1 micron polyester membrane, which was then added to a PCR, gave equivalent amplification to a nuclear pellet obtained from the same dilute volume by centrifugation. Quantification was performed by densitometric scans of ethidium bromide stained gels.

EXAMPLE 3

Hela cells were briskly freeze-thawed and exposed to a nuclei generating buffer composed as follows:

10 mM Tris pH 7.5
10 mM NaCl
3 mM $MgCl_2$
0.2% Triton X-100

Nuclei were captured via the DNA mesh/membrane mechanism described in Examples 1 and 2. The capture membrane was immersed in the lysis solution for 1–5 minutes at ambient temperature. Capture nuclei were processed in an identical manner as nuclei derived from blood. Successful capture of intact nuclei on DNA mesh was demonstrated and photographed. Digests were prepared and used to generate Southern blots in the manner described in Example 1.

The techniques described in these Examples have been successfully applied to human, goat, chicken, horse, rabbit, mouse and rat blood, to Hela and HL60 cell lines, and to rat kidney. All blood-derived samples were treated with the sucrose-triton lysis solution as in Example 1. Cell line and tissue-derived samples were treated with the sugarless lysis solution as in Example 3. In each case, capture of intact nuclei was demonstrated.

Capture membranes which have been used successfully are 1, 5, 6 and 11$\mu$ polyester woven membranes and 1$\mu$ nylon woven membrane. Either 1 $\mu$ membrane is preferred. Less preferred but effective to a lesser extent are 50, 100$\mu$ random mesh polycarbonate membranes and 5, 10$\mu$ track-etched polyester membranes. Also 0.45$\mu$ nitrocellulose has been used successfully, as has 0.45$\mu$ nylon, although the flow rate and hence washing efficiency were reduced.

We claim:

1. A method of separating components of cells, which method comprises
   a) treating a fluid containing whole cells so as to selectively lyse the cytoplasmic membrane together with a small proportion of the nuclear membranes but leaving a large proportion of the cell nuclei intact,
   b) applying the treated fluid to a surface whereby a mesh comprising DNA from the lysed nuclei is formed on the surface and captures intact cell nuclei,
   c) washing the mesh comprising DNA on the surface to separate the captured cell nuclei from other components of the cells.

2. The method as claimed in claim 1, wherein the fluid treated in step a) is mammalian blood.

3. The method as claimed in claim 1, wherein the surface is of a material which is capable of binding DNA.

4. The method as claimed in claim 1, wherein the surface is of polyester, polyamide, polycarbonate or cellulose.

5. The method as claimed in claim 1, wherein the surface is in the form of a permeable membrane.

6. The method as claimed in claim 5, wherein step b) is performed by passing the treated fluid through the permeable membrane whereby the mesh comprising DNA is formed on or in the permeable membrane and there captures intact cell nuclei.

7. The method as claimed in claim 5, wherein step c) is performed by passing a washing fluid through the permeable membrane.

8. The method as claimed in claim 1, wherein cell nuclei captured by the mesh comprising DNA are lysed and nucleic acids thereby exposed are treated or reacted in situ.

9. The method as claimed in claim 1, wherein a DNAse enzyme is used to release nuclei from the mesh comprising DNA on the surface.

* * * * *